(12) United States Patent
Wirtz et al.

(10) Patent No.: US 11,993,560 B2
(45) Date of Patent: May 28, 2024

(54) ALCOHOL SOLVENT RECOVERY AND PLANT OIL DECARBOXYLATION APPARATUS AND METHOD

(71) Applicant: MACH Technologies, Detroit, MI (US)

(72) Inventors: Robert N. Wirtz, Royal Oak, MI (US); Jason T. Wirtz, Royal Oak, MI (US); John W. Wirtz, II, Fort Gratiot, MI (US)

(73) Assignee: MACH Technologies, Detroit, MI (US)

( * ) Notice: Subject to any disclaimer, the term of this patent is extended or adjusted under 35 U.S.C. 154(b) by 40 days.

(21) Appl. No.: 17/242,388

(22) Filed: Apr. 28, 2021

(65) Prior Publication Data
US 2021/0363081 A1 Nov. 25, 2021

Related U.S. Application Data

(60) Provisional application No. 63/027,387, filed on May 20, 2020.

(51) Int. Cl.
*C07C 29/84* (2006.01)
*B01D 3/14* (2006.01)
(Continued)

(52) U.S. Cl.
CPC ............. *C07C 29/84* (2013.01); *B01D 3/145* (2013.01); *B01D 11/0288* (2013.01);
(Continued)

(58) Field of Classification Search
CPC ...... C07C 29/84; C07C 29/76; B01J 19/2475; B01J 19/2465; B01J 19/2445;
(Continued)

(56) References Cited

U.S. PATENT DOCUMENTS 2,109,157 A * 2/1938 Tijmstra ................... C11B 3/12
203/44
4,520,213 A 5/1985 Victor
(Continued)

OTHER PUBLICATIONS

International Search Report and Written Opinion for International Application No. PCT/US21/29337 dated Oct. 6, 2021 (23 pages).
(Continued)

*Primary Examiner* — Youngsul Jeong
(74) *Attorney, Agent, or Firm* — Reising Ethington P.C.

(57) ABSTRACT

A method of and apparatus for recovering an alcohol solvent from a liquid mixture of the solvent and plant oil and decarboxylating the plant oil may include, pressurizing the liquid mixture to a super-atmospheric pressure, recirculating the pressurized liquid mixture a plurality of times through at least one membrane separator to separate some of the solvent from the mixture to provide a concentrated mixture of the plant oil with less solvent, reducing the pressure of the liquid concentrated mixture to less than 15 psig, heating it at a pressure of less than 15 psig to a temperature sufficient to vaporize the solvent in the concentrated mixture, removing sufficient heat from the vaporized solvent to condense it to a liquid solvent at atmospheric pressure and temperature conditions, and heating the plant oil to a temperature desirably of at least 215° F. to decarboxylate the plant oil.

20 Claims, 2 Drawing Sheets

(51) Int. Cl.
  *B01D 11/02* (2006.01)
  *B01D 19/00* (2006.01)
  *B01D 61/18* (2006.01)
  *B01J 19/24* (2006.01)
  *C07C 29/76* (2006.01)

(52) U.S. Cl.
  CPC .......... *B01D 11/0296* (2013.01); *B01D 19/00* (2013.01); *B01D 61/18* (2013.01); *B01J 19/2445* (2013.01); *B01J 19/2465* (2013.01); *B01J 19/2475* (2013.01); *C07C 29/76* (2013.01); *B01J 2219/00087* (2013.01); *B01J 2219/00162* (2013.01)

(58) Field of Classification Search
  CPC .. B01J 2219/00087; B01J 2219/00162; B01D 11/0288; B01D 11/0296; B01D 3/145; B01D 61/18; B01D 19/00
  See application file for complete search history.

(56) References Cited

U.S. PATENT DOCUMENTS

| | | |
|---|---|---|
| 10,507,407 B2 | 12/2019 | Galyuk |
| 10,814,248 B2 | 10/2020 | Galyuk |
| 2004/0033280 A1 | 2/2004 | Whittle |
| 2010/0145117 A1 | 6/2010 | Seames et al. |
| 2012/0034667 A1 | 2/2012 | Kiuchi et al. |
| 2019/0241536 A1* | 8/2019 | Durkacz ............ B01D 11/0203 |
| 2019/0336521 A1* | 11/2019 | Kotra ................... A61K 31/775 |

OTHER PUBLICATIONS

International Preliminary Report on Patentability for International Application No. PCT/US2021/029337 dated Nov. 17, 2022 (13 pages).

* cited by examiner

ALCOHOL SOLVENT RECOVERY AND PLANT OIL DECARBOXYLATION APPARATUS AND METHOD

PRIORITY CLAIM

This application claims the priority of U.S. provisional patent application No. 63/027,387 filed on May 20, 2020 and the disclosure of which in its entirety is incorporated herein by reference.

TECHNICAL FIELD

This invention relates to the separation of an alcohol solvent such as ethanol from an alcohol and plant oil mixture and the decarboxylation of the plant oil and more particularly to an apparatus and method for doing so.

BACKGROUND

Many industrial, cosmetic, medical, drug and pharmacological processes and products use oils and compounds extracted from plant material. Various processes and apparatus for extracting these so-called essential oils or plant oils have been developed which use an alcohol solvent such as ethanol to extract the plant oil from the plant material which produces an ethanol and plant oil mixture from which the ethanol is separated usually for reuse and the separated plant oil is decarboxylated to produce a so called "finished" plant oil. The primary commercial way of separating the ethanol and plant oil is to use a falling or rising film evaporator which requires heating of the mixture to evaporate the solvent and cooling it to liquid form. Typically to decarboxylate the separated plant oil it is transferred to a vessel and heated usually at atmospheric pressure to a high temperature of about 280 to 300° F. for a long period of time of about 50 to 80 minutes. These processes require a lot of thermal energy and typically are done in manually cycled apparatus in operator manipulated and monitored batches which is labor intensive and thus expensive and may produce undesirably varying results.

SUMMARY

In at least some implementations, a method of recovering an alcohol solvent from a liquid mixture of the solvent and plant oil and decarboxylating the plant oil may include pressurizing the liquid mixture to a super-atmospheric pressure, recirculating the pressurized liquid mixture a plurality of times through the at least one membrane separator to separate some of the solvent from the mixture to provide a concentrated mixture of the plant oil with less solvent in the concentrated mixture, reducing the pressure of the liquid concentrated mixture to less than 15 psig, heating the liquid concentrated mixture at a pressure of less than 15 psig to a temperature sufficient to vaporize the solvent in the mixture, removing sufficient heat from the vaporized solvent to condense it to a liquid solvent at atmospheric pressure and temperature conditions, and heating the plant oil to a temperature of at least 215° F. to decarboxylate the plant oil. In at least some implementations the liquid mixture may be pressurized to at least 500 psig and recirculated through the at least one membrane separator a sufficient number of times for the liquid mixture to have a ratio by volume of not more than 5 parts of solvent to one part of plant oil. In at least some implementations, the liquid concentrated mixture may be heated in a reactor to vaporize the solvent in the mixture and also may apply a vacuum to the reactor to remove the vaporized solvent from the reactor. In at least some implementations, the liquid concentrated mixture may be heated to a temperature of at least 150° F. and passed into the reactor, and in the reactor may be heated to a higher temperature to vaporize substantially all of the solvent in the concentrated mixture, the vaporized solvent may be removed from the reactor and the remaining plant oil heated in the reactor to a high enough temperature which may be at least 215° F. for a period of time of at least 15 minutes to decarboxylate the plant oil.

In at least some implementations, an apparatus for recovering an alcohol solvent from a mixture of the solvent and plant oil and decarboxylating the plant oil may include at least one tank to receive the liquid mixture, at least one membrane separator to separate at least some of the solvent from the liquid mixture to provide a concentrated mixture with less solvent therein, a pump to circulate the liquid mixture through the at least one separator and the at least one tank a plurality of times, a reactor to heat the concentrated mixture to a temperature high enough to vaporize substantially all of the solvent in it and to a temperature high enough to decarboxylate the plant oil; and a heat exchanger to decrease the temperature of the vaporized solvent sufficiently to condense it to be a liquid at atmospheric pressure and temperature. In at least some implementations, the pump may supply the mixture to the at least one membrane separator at a pressure of at least 500 psig. In at least some implementations, a pressure reducer may decrease the pressure of the liquid mixture downstream of the at least one membrane and through the tank to a pressure not greater than substantially 15 psig. In at least some implementations, the pump may recirculate the liquid mixture through the at least one membrane separator at least until the ratio by volume in the concentrated mixture of the solvent to the plant oil is not greater than 5 parts solvent to 1-part plant oil. In at least some implementations, a heat exchanger downstream of the at least one membrane and upstream of the pump may remove heat from the circulating liquid mixture and may decrease its temperature by at least 9° F. In at least some implementations, a heat exchanger may heat to an elevated temperature the concentrated mixture supplied to the reactor.

In at least some implementations, a vacuum pump may apply a vacuum to the reactor and the heat exchanger to facilitate flow of the vaporized solvent from the reactor and into this heat exchanger. In at least some implementations, the vacuum pump may also apply a vacuum to a solvent tank to receive liquid solvent from the heat exchanger. At least some implementations may include a recovered solvent tank to receive the separated liquid solvent from the at least one membrane separator and/or liquid solvent from the solvent tank. In at least some implementations, the at least one tank may include a first tank and a second tank each configured to alternate with the other to supply a separate batch of liquid mixture of solvent and plant oil to the pump for circulation of such batch through the at least one membrane and the tank associated with such batch.

BRIEF DESCRIPTION OF THE DRAWINGS

The following detailed description of certain embodiments and best mode will be set forth with reference to the accompanying drawings in which.

DETAILED DESCRIPTION OF THE PREFERRED EMBODIMENTS

In at least some applications a method of separation of an alcohol solvent, such as ethanol, from a liquid ethanol and plant oil mixture may include pressurizing the liquid mixture at ambient temperature to a pressure in the range of 500 to 800 psi, passing the pressurized mixture through at least one membrane separator a plurality of times to separate part of the ethanol from the mixture, heating to an elevated temperature the mixture from which some of the solvent has been removed to vaporize substantially all of the rest of the solvent from the mixture, and separating and condensing the vaporized solvent to be a liquid at atmospheric pressure and temperature. In at least some applications, the initial mixture (before recirculation) may have about 95 to 15 parts of ethanol to 1-part of plant oil by volume. In some applications the mixture may be passed through the at least one membrane separator a sufficient number of times to separate sufficient solvent so that the resulting condensed mixture may have 2 to 5 parts of solvent to 1-part of plant oil by volume before the resulting condensed mixture is heated to an elevated temperature to vaporize substantially all of the rest of the solvent from the mixture. In at least some applications, at least some of the heat produced by pressurizing the mixture may be removed from the mixture preferably by cooling at least some of the mixture before it is heated to an elevated temperature to separate further solvent from the mixture.

In at least some applications, the method may include decarboxylation of the separated plant oil by heating it to a temperature of at least 215° F. in a partial vacuum for at least 20 minutes. In at least some applications, the plant oil may be heated to a temperature in the range of 215 to 275° F. in a vacuum of at least 20 mm of mercury for a time usually in the range of 20 to 80 minutes. In at least some applications, the plant oil may be agitated or stirred while it is being heated.

Figure 1:
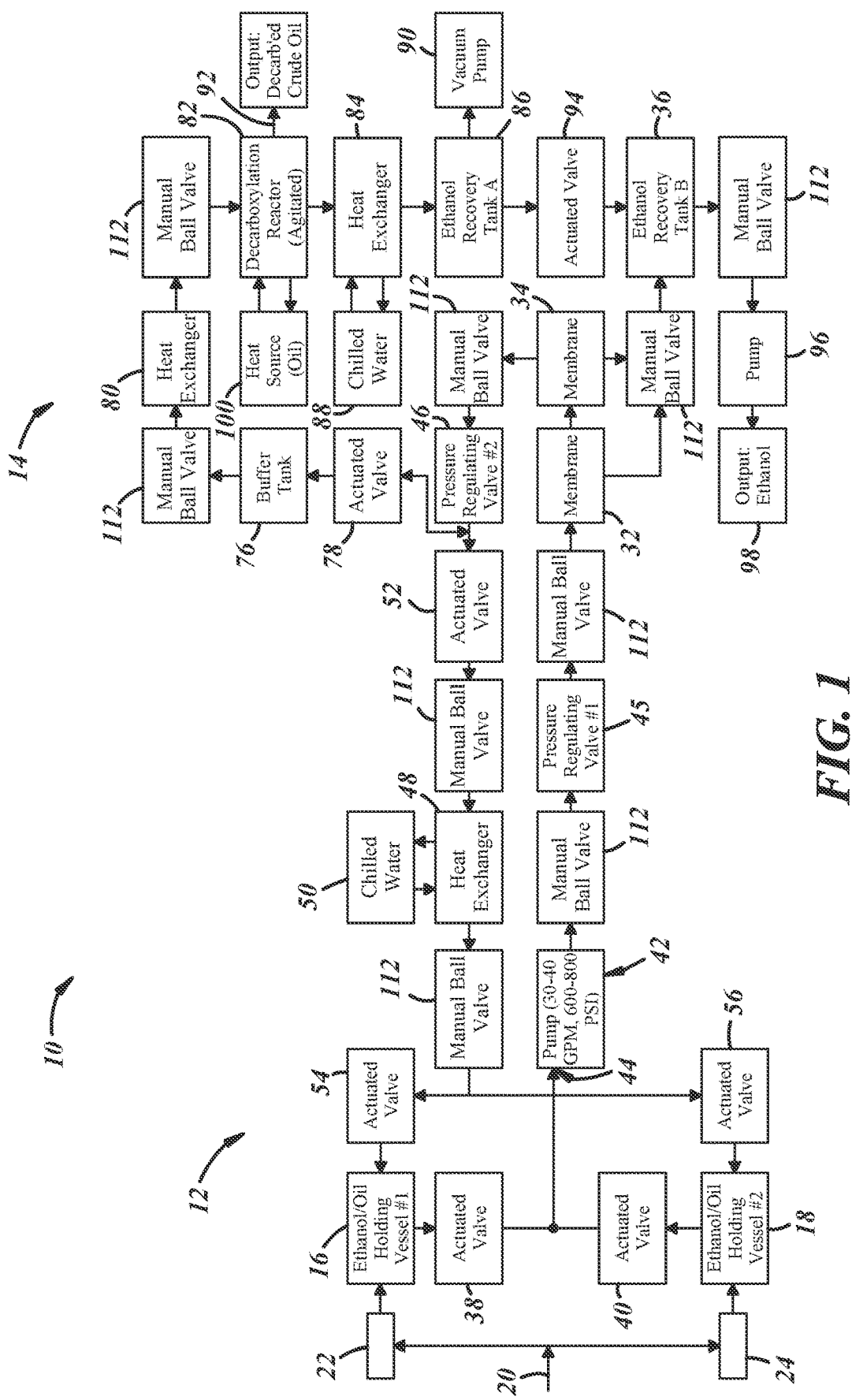
FIG. 1 is a schematic drawing of an apparatus for solvent recovery from a solvent and plant oil mixture and for decarboxylation of the separated plant oil.
Figure 3:
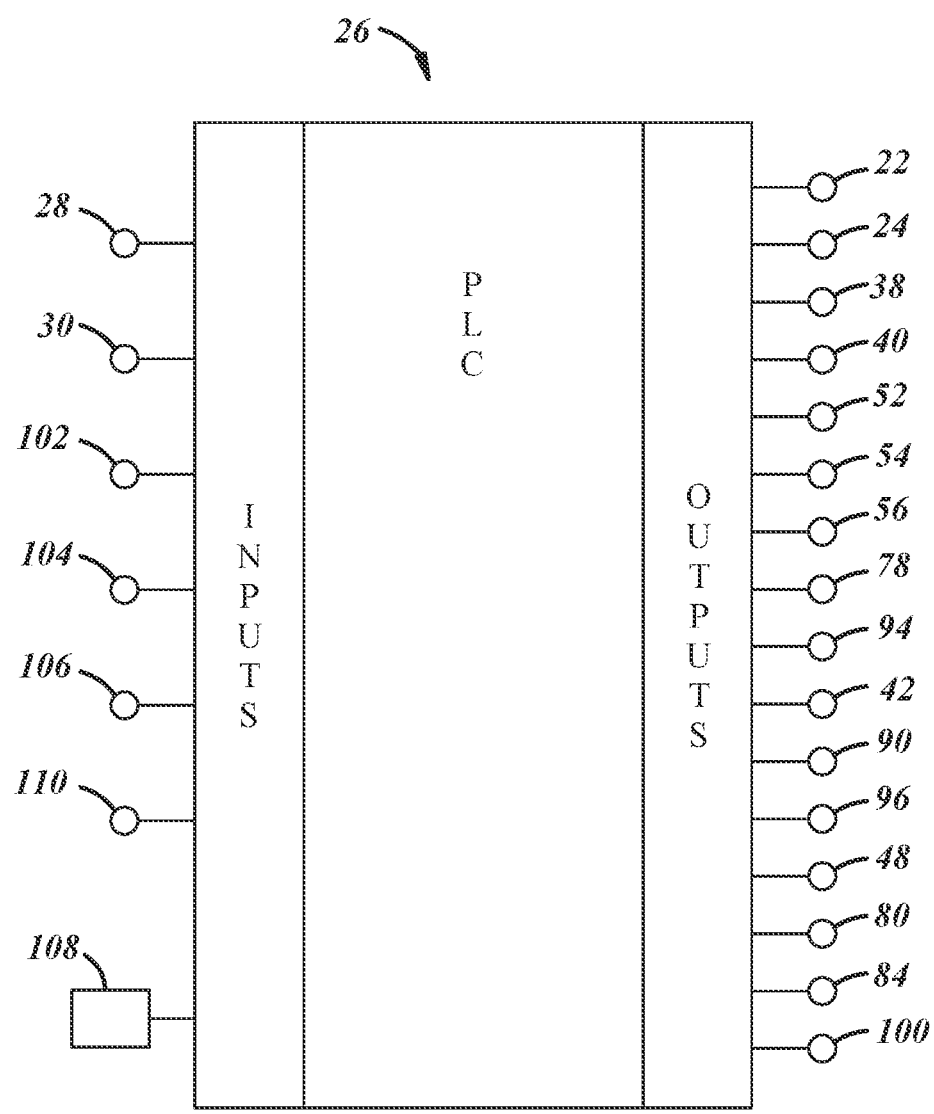
FIG. 3 is a schematic of part of a sensor and control system of the apparatus of FIG. 1.

As shown FIG. 1, in at least some applications a solvent recovery and plant oil decarboxylation apparatus 10 may include a first recirculation portion 12 which separates and recovers only some of an alcohol solvent such as ethanol from an ethanol and plant oil mixture and a second portion 14 which separates and recovers substantially all of the rest of the solvent from the mixture and may decarboxylate the separated plant oil to provide a finished plant oil. The recirculation portion 12 may include at least one tank and desirably first and second tanks 16 & 18 for holding an alcohol solvent and plant oil mixture 20 (herein after sometimes referred to as an ethanol and plant oil mixture or an ethanol and oil mixture or the mixture) which mixture may be supplied from an upstream source to each tank through an associated solenoid actuated shut off valve 22 or 24 which may be controlled by an electronic controller such as a programmable logic controller (PLC) 26 [FIG. 3] receiving a signal from a separate level sensor 28 or 30 associated with each tank to indicate when a desired full or "high" level of mixture in the tank has been reached. These tanks may hold the mixture 20 as a liquid at substantially ambient atmospheric pressure and temperature.

If the apparatus has both a first tank 16 and a second tank 18, the recirculation cycle will be performed with only one tank at a time and may alternate between one tank and the other after completion of each recirculation cycle. For example, if the apparatus begins operation with a full tank 16, the mixture 20 therein may be recirculated through at least one and desirably two or more membrane separators 32 and 34 a plurality of times since each separator may separate only part of the ethanol from the mixture with each pass of the mixture through the separator. This separated ethanol is in liquid state and may be transferred to a holding tank 36. For recirculation, liquid mixture 20 may be supplied from the tank 16 through an associated solenoid actuated outlet shutoff valve 38 (or alternately for tank 18 through an associated solenoid shutoff valve 40) to a pump 42 and returned to and through this tank 16 to the inlet 44 of the pump. The pressure at which the pump supplies mixture to the membrane separators may be controlled and regulated by a pressure regulator 45.

Mixture from the membrane separator 34 may be returned to its associated recirculating tank 16 or 18 through a pressure reducing valve 46 and desirably a heat exchanger 48. This valve 46 desirably decreases its outlet mixture pressure to less than 15 psig so that the components downstream of this valve and upstream of the pump inlet 44 do not have to be of a pressure rated construction. The heat exchanger 48 may cool the returning mixture to remove at least some of the heat from the mixture produced by the pump pressurizing the mixture to ensure the ethanol in the mixture remains in a liquid state. Cooling the temperature of mixture by about 9 to 13° F. each time it passes through this heat exchanger is believed to be sufficient. To do so, a suitable cooling fluid such as chilled water may be supplied to the heat exchanger by a chiller 50. The mixture inlet of this heat exchanger may be connected to the outlet of the pressure reducer valve 46 through a solenoid actuated shutoff valve 52 and the mixture outlet of this heat exchanger may be connected to an inlet of the tank 16 through an associated shutoff valve 54 (or alternately to an inlet of the tank 18 through an associated solenoid actuated shutoff valve 56). The pump 42 may supply the mixture to the at least one and preferably the two or more membrane separators 32 & 34 at a super-atmospheric pressure typically in the range of 500 to 900 psig and desirably 600 to 800 psig and at a flow rate typically in the range of 25 to 45 and desirably 30 to 40 gallons per minute (gpm). A suitable pump 42 is commercially available from Wanner Engineering Inc. of 1204 Chestnut Avenue, Minneapolis, MN 55403 as a Hydra-cell D35 Series pump.

Figure 2:
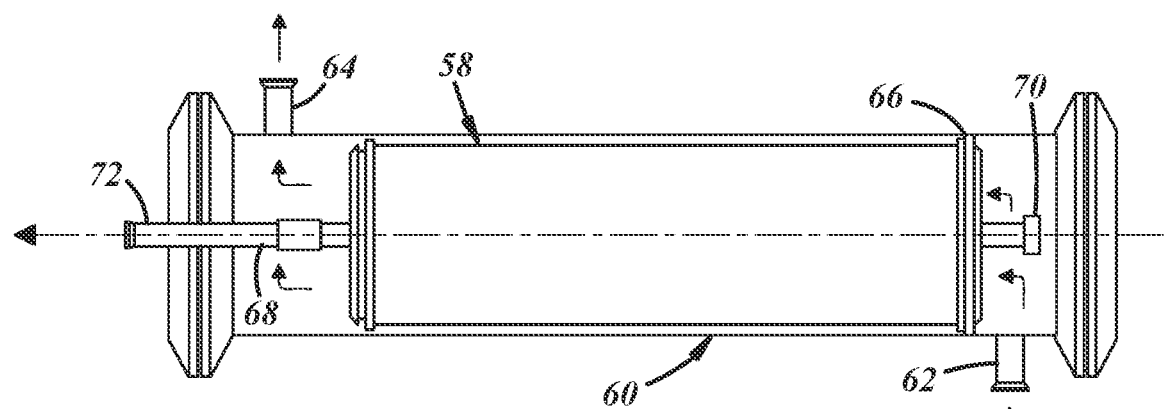
FIG. 2 is a schematic drawing of a membrane filter of the apparatus of FIG. 1.

As shown in FIG. 2, each of the membrane separators 32 & 34 may include a module 58 with a coiled or spiral wound membrane received in a high pressure resistant cylindrical housing 60 with a mixture feed inlet 62 and a mixture retentate outlet 64. The membrane module 58 may be sealed at the inlet end to the housing by an annular seal 66 and may have a center tube 68 with a cap 70 at one end and extending through an end of the housing to provide and ethanol permeate outlet 72. Suitable membrane modules are commercially available from Evonik Industries AG of North Rhine-Westpathalia, Essen, Germany as DuraMem membrane module 8040.

In operation, the ethanol and oil mixture is recirculated through the membrane separators 32 & 34 until the mixture reaches a desired concentration or ratio such as about 5 and desirably 3 to 4 parts of ethanol to 1 part of oil by volume which may be determined by the PLC using a signal from the level sensor 28 or 30 associated with the tank 16 or 18 through which the mixture is being recirculated and comparing the initial "high" level for such tank with the current lower level of the mixture therein. When a desired low level of the recirculating mixture is reached (thereby indicating the desired mixture concentration ratio), the concentrated mixture may be transferred to a buffer or holding tank 76 for further processing by the second portion 14 of the apparatus 10 by the PLC 26 opening a normally closed solenoid actuated shut off valve 78 and closing the solenoid actuated valve 52. Once all of the recirculating concentrated mixture has been pumped from the associated tank 16 or 18 through which it was recirculated as indicated by a signal from its associated level sensor 28 or 30 to the PLC 26 and transferred to the holding tank 76, the PLC may close the solenoid actuated valves 78, 54 and 38. To refill the tank 16 with another fresh ethanol and oil mixture the PLC also may open the solenoid actuated valve 22.

If the tank 18 is full or at a "high" level as indicated by its associated level sensor 30 of a fresh ethanol and oil mixture, the PLC 26 may confirm the solenoid valves 24, 38 & 54 are closed and if so, may open the solenoid actuated valves 40 & 56 and energize the pump 42 to begin recirculation of a batch of fresh mixture from this tank 18 through the membrane separators 32 & 34 to produce another batch of concentrated mixture and then transfer it to the holding tank 76 in the same way as described for tank 16. In this way, a batch of fresh ethanol and plant oil mixture from one and then the other of the tanks 16 and 18, one at a time may be processed substantially continuously to provide one batch after another of concentrated mixture, which may be transferred to the holding tank 76 for further processing by the second portion 14 of the apparatus 10.

In the second portion 14 of the apparatus 10, concentrated liquid mixture from the holding tank 76 may be pumped desirably at a pressure of less than 15 psig through a pre-heat heat exchanger 80 and into a reactor assembly 82 for evaporation of the remaining solvent and decarboxylation of the plant oil. The heat exchanger 80 may preheat the concentrated mixture to a temperature in the range of about 150 to 175° F. before it enters the reactor assembly. Heat may be supplied to this heat exchanger by any suitable means such as by a heated fluid medium such as heated water, oil, air, etc. In a chamber of the reactor assembly 82 the mixture may be initially heated to a temperature in the range of about 150 to 225° F. to convert the remaining ethanol to a vapor form which may be passed through a heat exchanger 84 to condense it to liquid ethanol which may be received in a recovery tank 86. To do so, a cooling medium such as chilled water provided by a chiller 88 may be circulated through one side if this heat exchanger. To assist the flow of the ethanol vapor from the reactor assembly, through the heat exchanger and the condensed liquid ethanol into the recovery tank 86, a vacuum may be applied to this tank by a vacuum pump 90. This vacuum may also lower the temperature at which the ethanol evaporates in the reactor assembly. It is believed the time required to evaporate the remaining ethanol may be decreased by agitating or stirring the mixture in the chamber by a suitable agitator such as a rotating blade or propeller therein to promote rapid heating of the mixture and a more uniform temperature throughout the mixture as it is being heated in the reactor chamber. In theory this agitation or stirring produces forced convection heat transfer to the mixture.

After the ethanol has been evaporated and removed from the reactor assembly 82, decarboxylation of the plant oil which remains therein may be started. Depending on the composition of the plant oil, its decarboxylation may occur by raising and maintaining its temperature in the reactor assembly to about 215 to 275° F. for a period of time which may be at least 15 minutes and usually may be in the range of about 20 to 80 minutes and desirably under a vacuum of at least 20 mm of mercury which may be produced by the vacuum pump 90. The plant oil may be agitated or stirred in the reactor chamber to promote rapid heating of the mixture and a more uniform temperature throughout the mixture. After decarboxylation of the plant oil is complete, the vacuum may be relieved and the decarboxylated or so called "finished" plant oil 92 removed from the reactor assembly. The rate of removal of the finished plant oil may be increased by applying a dry or moisture free inert gas to the interior of the chamber at a low pressure such at 1 to 5 psig. Also, after the vacuum is relieved, the recovered liquid ethanol in the tank 86 may be transferred to tank 36 by opening the normally closed solenoid actuated valve 94 and if need be by actuating a pump 96. Also, by actuating the pump 96, recovered liquid ethanol may be supplied from the recovery tank 36 such as for substantially immediate reuse and/or storage in a tank 98 desirably with a moisture free or inert atmosphere therein before reuse.

The reactor assembly 82 may be heated to the desired temperatures by any suitable source such as a source 100 of heated oil circulated through the reactor assembly to heat the mixture received in the chamber of the reactor assembly. After the finished plant oil is removed from the reactor assembly, its chamber may be cooled to at least the desired lower temperature for receiving a new batch of concentrated ethanol and oil mixture and the cycle of the second portion 14 of the apparatus 10 may be repeated with a new batch of the concentrated mixture transferred from the holding tank 76.

In at least some applications, operation of the apparatus 10 may be automated by the PLC 26 (FIG. 3) cycling and controlling operation of the various components including the solenoid actuated valves 22, 24, 38, 40, 52, 54, 56, 78 and 94, and pumps 42, 90, and 96. If desired the PLC also may control the operating temperatures of the heat exchangers 48, 80, and 84 such as by using a signal from a respectively associated temperature sensor 102, 104 and 106. The desired operating temperatures and associated time periods for the reactor assembly may be predetermined for a particular composition of the concentrated ethanol and oil mixture and put into a memory of the PLC 26 such as by a human machine interface (HMI) 108, computer, tablet or the like. A temperature sensor 110 could be associated with the reactor assembly to provide a signal used by the PLC to adjust and control the heat source 100 for the reactor assembly to maintain its predetermined temperatures. Of course, persons of ordinary skill could design and implement a variety of different schemes and devices for automating the operation of the apparatus 10.

To facilitate service, maintenance, repair and replacement of various components of the apparatus, manual shutoff valves which are normally open such as ball valves 112 may be included in the apparatus.

The forms of the invention disclosed herein constitute presently preferred embodiments and many other forms and embodiments are possible and will occur to persons skilled in the art. It is not intended herein to mention all of the possible equivalent forms or ramifications of the invention. Rather it is understood that the terms used herein are merely descriptive, rather than limiting, and that various changes may be made without departing from the spirit or scope of the invention which is particularly desirable for efficiently and economically recovering an alcohol solvent such as ethanol from an ethanol and plant oil mixture for reuse of the recovered ethanol and the decarboxylation of the plant oil.

The invention claimed is:

1. An apparatus for recovering an alcohol solvent from a mixture of the solvent and plant oil and decarboxylation of the plant oil, the apparatus comprising;
at least one tank configured to receive a liquid mixture of an alcohol solvent and plant oil;
at least one membrane separator configured to separate at least some of the solvent from the liquid mixture when flowing through the at least one membrane separator to provide a concentrated mixture with less solvent therein compared to the liquid mixture, wherein the at least one membrane separator further comprises a coiled or spiral wound membrane received in a super-atmospheric pressure resistant cylindrical housing, the cylindrical housing being resistant to a super-atmospheric pressure of at least 500 psig;
a pump configured to circulate the liquid mixture through the at least one membrane separator and the at least one tank a plurality of times, wherein the pump is configured to supply the liquid mixture to the at least one membrane separator at a pressure of at least 500 psig;
a reactor configured to heat the concentrated mixture to a temperature high enough to vaporize substantially all of the solvent in the concentrated mixture and to a temperature high enough to decarboxylate the plant oil;
a heat exchanger configured to decrease the temperature of the vaporized solvent sufficiently to condense it to be a liquid at atmospheric pressure and temperature; and
an actuated outlet valve associated with the at least one tank, through which the liquid mixture is supplied from the at least one tank through the actuated outlet valve to the pump and the liquid mixture is returned to and through the at least one tank to an inlet of the pump.

2. The apparatus of claim 1 which also comprises a pressure reducer configured to decrease the pressure of the concentrated mixture downstream of the at least one membrane separator and through the at least one tank to a pressure not greater than 15 psig.

3. The apparatus on claim 1 which also comprises a heat exchanger downstream of the at least one membrane separator and upstream of the pump which is configured to remove heat from the concentrated mixture.

4. The apparatus of claim 3 wherein the heat exchanger is configured to decrease the temperature of the concentrated mixture flowing through it by at least 9° F.

5. The apparatus on claim 1 wherein the pump is configured to recirculate the liquid mixture through the at least one membrane separator at least until a ratio by volume in the concentrated mixture of the solvent to the plant oil is not greater than 5 parts solvent to 1 part plant oil.

6. The apparatus of claim 1 which also comprises a vacuum pump configured to apply a vacuum to the reactor and the heat exchanger to facilitate flow of the vaporized solvent from the reactor and into the heat exchanger.

7. The apparatus of claim 1 which also comprises a solvent tank configured to receive liquid solvent from the heat exchanger downstream of the reactor, and a vacuum pump configured to apply a vacuum to the reactor, the heat exchanger, and the solvent tank to facilitate the flow of vaporized solvent from the reactor into this downstream heat exchanger and liquid solvent from this downstream heat exchanger into the solvent tank.

8. The apparatus of claim 1 which also comprises another pump configured to transfer liquid solvent from the solvent tank.

9. The apparatus of claim 1 which also comprises a recovered solvent tank configured to receive the separated liquid solvent from the at least one membrane separator.

10. The apparatus of claim 7 which also comprises a recovered solvent tank configured to receive the separated liquid solvent from the at least one membrane separator and receive liquid solvent from the solvent tank configured to receive liquid solvent from the heat exchanger.

11. The apparatus of claim 1 which also comprises a heat exchanger configured to heat to an elevated temperature the concentrated mixture supplied to the reactor.

12. The apparatus of claim 1 which also comprises a recovered solvent tank configured to receive the separated liquid solvent from the at least one membrane separator and receive liquid solvent from a solvent tank configured to receive liquid solvent from the heat exchanger.

13. The apparatus of claim 1 which also comprises a pressure reducer downstream of the at least one membrane separator configured to decrease a pressure of the concentrated mixture to not greater than 15 psig and a tank downstream of the pressure reducer and upstream of the reactor configured to receive the concentrated mixture from the pressure reducer.

14. The apparatus of claim 1 wherein the reactor is configured for heating the plant oil therein to a temperature of at least 215° F. for decarboxylation of the plant oil.

15. The apparatus of claim 1 wherein the at least one tank comprises a first tank and a second tank each configured to alternate with the other to supply a separate batch of liquid mixture of solvent and plant oil to the pump for circulation of such batch through the at least one membrane separator and the tank associated with such batch.

16. The apparatus of claim 1, wherein the reactor is configured to first heat the concentrated mixture to a temperature high enough to vaporize substantially all of the solvent and then configured to heat the plant oil to a temperature high enough to decarboxylate the plant oil.

17. A method of recovering an alcohol solvent from a mixture of the solvent and plant oil and decarboxylating the plant oil by using the apparatus recited in claim 1 comprising:
pressurizing a liquid mixture of an alcohol solvent and plant oil to a super-atmospheric pressure of at least 500 psig;
recirculating the pressurized liquid mixture, a plurality of times through at least one membrane separator to separate some of the solvent from the mixture to provide a liquid concentrated mixture of the plant oil with less solvent in the concentrated mixture;
reducing the pressure of the liquid concentrated mixture to less than 15 psig;
heating the liquid concentrated mixture at a pressure of less than 15 psig to a temperature sufficient to vaporize the solvent in the liquid concentrated mixture;
removing sufficient heat from the vaporized solvent to condense the vaporized solvent to be a liquid solvent at atmospheric pressure and temperature conditions; and
heating the plant oil resulted from the liquid concentrated mixture after removing the vaporized solvent to a temperature of at least 215° F. to decarboxylate the plant oil.

18. The method of claim 17 wherein the pressurized liquid mixture is recirculated through the at least one membrane separator a sufficient number of times for the liquid mixture to have a ratio by volume of not more than 5 parts of solvent to 1 part of plant oil.

19. The method of claim 17 wherein the liquid concentrated mixture is heated in a reactor to vaporize the solvent in the mixture and also comprises applying a vacuum to the reactor to remove the vaporized solvent from the reactor.

20. The method of claim 17 which also comprises heating the liquid concentrated mixture to a temperature of at least 150° F. and passing it into a reactor, in the reactor heating the liquid concentrated mixture to a higher temperature to vaporize substantially all of the solvent in the liquid concentrated mixture, removing the vaporized solvent from the reactor and heating the plant oil remaining in the reactor to a high enough temperature for a period of time of at least 15 minutes to decarboxylate the plant oil.

\* \* \* \* \*